United States Patent
Lee et al.

(10) Patent No.: US 11,771,610 B2
(45) Date of Patent: Oct. 3, 2023

(54) TENT-TYPE MOBILE INFECTIOUS DISEASE CLINIC

(71) Applicants: INDUSTRY-ACADEMIC COOPERATION FOUNDATION, YONSEI UNIVERSITY, Seoul (KR); SEOUL NATIONAL UNIVERSITY R&DB FOUNDATION, Seoul (KR); KOREA ENGINEERING & CLEAN TECHNOLOGY CO., LTD., Gangwon-do (KR)

(72) Inventors: Kwang Suk Lee, Seoul (KR); Kyo Chul Koo, Seoul (KR); Hyung Min Park, Seoul (KR); Joo Yeon Park, Seoul (KR); Ye Eun Kang, Seoul (KR); Seok Gyu Park, Gyeonggi-do (KR); Dae Sick Choi, Gyeonggi-do (KR); Seon Il Kim, Gyeonggi-do (KR); Sun Ju Lee, Gyeonggi-do (KR)

(73) Assignees: INDUSTRY-ACADEMIC COOPERATION FOUNDATION, YONSEI UNIVERSITY, Seoul (KR); SEOUL NATIONAL UNIVERSITY R&DB FOUNDATION, Seoul (KR); KOREA ENGINEERING & CLEAN TECHNOLOGY CO., LTD., Gangwon-do (KR)

( * ) Notice: Subject to any disclaimer, the term of this patent is extended or adjusted under 35 U.S.C. 154(b) by 21 days.

(21) Appl. No.: 17/674,589

(22) Filed: Feb. 17, 2022

(65) Prior Publication Data
US 2022/0257444 A1    Aug. 18, 2022

(51) Int. Cl.
*A61G 10/00* (2006.01)
*A61G 10/02* (2006.01)
*A61L 2/10* (2006.01)

(52) U.S. Cl.
CPC ......... *A61G 10/005* (2013.01); *A61G 10/023* (2013.01); *A61L 2/10* (2013.01)

(58) Field of Classification Search
CPC .. A61G 10/00–04; A62B 31/00; A62B 29/00; A61L 2202/122; A61L 2202/16;
(Continued)

(56) References Cited

U.S. PATENT DOCUMENTS

2004/0074212 A1*  4/2004  Yachi ............... B01D 46/0016
                                                   55/385.2
2016/0074268 A1*  3/2016  Breegi ............... A61G 11/009
                                                   600/21
(Continued)

FOREIGN PATENT DOCUMENTS

JP       5475319 B2      4/2014
KR     200406536 Y1      1/2006
(Continued)

OTHER PUBLICATIONS

Office Action issued in corresponding KR Application No. 10-2021-0021961, dated Feb. 10, 2022, and an English Translation, 16 pages.
(Continued)

*Primary Examiner* — Thaddeus B Cox
(74) *Attorney, Agent, or Firm* — Burris Law, PLLC

(57) ABSTRACT

The present disclosure relates to a tent-type mobile infectious disease clinic, and more particularly, to a mobile infectious disease clinic, which is a tent-type mobile infectious disease clinic that makes it possible to promptly install a large number of mobile infectious disease clinics due to having mobility and being easy to install and remove, that allows a test subject to be tested by a healthcare provider using an infectious disease test kit while the test subject is isolated in the tent-type mobile infectious disease clinic, the healthcare provider is outside the tent-type mobile infectious
(Continued)

disease clinic, and exposure of the body parts is minimized, that performs sterilization of an infectious disease using an ultraviolet C (UV-C) lamp to reduce the time taken for disinfecting the clinic, and that allows the light radiation intensity of the UV-C lamp to be adaptively adjusted according to the body temperature of the test subject.

4 Claims, 8 Drawing Sheets

(58) Field of Classification Search
CPC ..... A61L 2202/25; A61B 90/05; A61B 90/40; A61B 2090/401
See application file for complete search history.

(56) References Cited

U.S. PATENT DOCUMENTS

2021/0236366 A1* 8/2021 Serrano ............... A61F 7/0053
2021/0315758 A1* 10/2021 Bui ..................... A61G 10/02

FOREIGN PATENT DOCUMENTS

KR   101575233 B1   12/2015
KR   102165792 B1   10/2020

OTHER PUBLICATIONS

Notice of Allowance issued in corresponding KR Application No. 10-2021-0021961, dated Jun. 28, 2022, and an English translation, 5 pages.
Office Action issued in corresponding KR Application No. 10-2021-0021959, dated Feb. 10, 2022, and an English translation thereof, 18 pages.
Winicare Co., Ltd., Introducing the Smart Negative Pressure Room and English Translation information pages, https://blog.naver.com/winicare0201/222010755133 (accessed Feb. 4, 2022), 20 pages.

* cited by examiner

TENT-TYPE MOBILE INFECTIOUS DISEASE CLINIC

CROSS-REFERENCE TO RELATED APPLICATION

This application claims priority to and the benefit of Korean Patent Application No. 10-2021-0021961, filed on Feb. 18, 2021, the disclosure of which is incorporated herein by reference in its entirety.

BACKGROUND

1. Field

The present disclosure relates to a tent-type mobile infectious disease clinic, and more particularly, to a mobile infectious disease clinic, which is a tent-type mobile infectious disease clinic that makes it possible to promptly install a large number of mobile infectious disease clinics due to having mobility and being easy to install and remove. The tent-type mobile infectious disease clinic allows a test subject to be tested by a healthcare provider using an infectious disease test kit while the test subject is isolated in the tent-type mobile infectious disease clinic and while the healthcare provider is outside the tent-type mobile infectious disease clinic. The tent-type mobile infectious disease clinic minimizes exposure of the body parts, performs sterilization of an infectious disease using an ultraviolet C (UV-C) lamp to reduce the time taken for disinfecting the clinic, and allows the light radiation intensity of the UV-C lamp to be adaptively adjusted according to the body temperature of the test subject.

2. Discussion of Related Art

In recent years, the spread of infectious diseases such as Severe Acute Respiratory Syndrome (SARS), Middle East Respiratory Syndrome (MERS), and Coronavirus disease has become a social problem. When an infectious disease spreads, healthcare providers should repeatedly perform testing to determine whether a number of test subjects are infected. Therefore, typical medical facilities alone are not sufficient to test a large number of test subjects, and mobile clinics for testing a large number of test subjects are installed.

However, in the mobile clinic installed with a tent or the like, disinfection of the clinic performed after each testing usually takes 10 to 30 minutes, which is not a small amount of time. In addition, there are problems in that a considerable amount of money and time is utilized and the physical strength of a healthcare provider is exhausted in a process in which the healthcare provider changes into a new protective suit after each testing.

If disinfection and disinfection completion notification can be performed automatically after testing, the time taken for disinfection of the clinic can be efficiently utilized. Further, if testing can be performed while a healthcare provider and a test subject are isolated and exposure of the body parts is minimized, it is possible to save time, cost, and physical strength of the healthcare provider that are utilized by the healthcare provider to change into a new protective suit after each testing.

Therefore, there is a need for a mobile infectious disease clinic that allows a test subject to be tested by a healthcare provider using an infectious disease test kit while the healthcare provider and the test subject are isolated and that allows disinfection and disinfection completion notification to be automatically performed after testing.

Also, in order to prevent the external spread of an infectious disease, the mobile infectious disease clinic includes a negative pressure device. The negative pressure device is a device that makes the air pressure inside the clinic lower than the air pressure outside the clinic to cause the air outside the clinic to enter the clinic and filters and discharges the air inside the clinic. In order to prevent the spread of an infectious disease, the negative pressure should be maintained above a predetermined value. In the case of a patient with fever, etc. who is likely to be tested positive for the disease, if it is possible to adaptively adjust the negative pressure so that the negative pressure can be increased to be higher than usual, there is no need to set the output of the negative pressure device to be high at all times, and thus the negative pressure device can be efficiently operated.

Therefore, there is a need for a mobile infectious disease clinic that allows the internal negative pressure to be adaptively adjusted according to the body temperature of the test subject.

Also, if a mobile infectious disease clinic cluster including a plurality of mobile infectious disease clinics is present, and disinfection and indication of whether disinfection is completed are automatically performed in each mobile infectious disease clinic, a healthcare provider may perform testing in a clinic that is disinfected and available, and thus the time taken for disinfection of the plurality of mobile infectious disease clinics may be efficiently used. Also, by continuously providing an available mobile infectious disease clinic, the number of tests performed can be maximized using the least possible number of healthcare providers within a limited amount of time.

Therefore, there is a need for a mobile infectious disease clinic in which disinfection and indication of whether disinfection is completed are automatically performed.

Also, if an ultraviolet C (UV-C) lamp, which is harmless to the human body and has a sterilizing effect, is used in a mobile infectious disease clinic, sterilization of an infectious disease can be effectively performed while testing is performed or disinfection is performed, and the time taken for disinfection can be reduced. In the case of a patient with fever, etc. who is likely to be tested positive for the disease, if it is possible to adaptively adjust the light radiation intensity of the UV-C lamp so that the light radiation intensity can be increased to be higher than usual, there is no need to set the output of the UV-C lamp to be high at all times, and thus the UV-C lamp can be efficiently operated. Also, when an abnormality occurs in the negative pressure device, if the output of the UV-C lamp is increased, sterilization can be performed before the infectious disease spreads outside the clinic, and thus the spread of the infectious disease through air can be minimized.

Therefore, there is a need for a mobile infectious disease clinic that includes a UV-C lamp capable of effectively performing sterilization of an infectious disease, reducing the disinfection time, and adaptively adjusting the light radiation intensity according to whether the body temperature of the test subject is abnormal or the negative pressure device is abnormal.

In addition, if a mobile infectious disease clinic is provided in the form of a tent, the mobile infectious disease clinic may have mobility and be easy to install and remove, and thus, in a case where it is difficult for a number of test subjects to directly visit a medical institution or a number of test subjects are suspected of having the disease but are self-isolated due to medical institutions being fully occupied, by promptly installing a large number of mobile infectious disease clinics, testing for an infectious disease can be actively performed. Increasing the number of tests performed is effective in preventing the spread of the disease.

Therefore, there is a need for a tent-type mobile infectious disease clinic.

RELATED ART DOCUMENT

Patent Document (Patent Document 0001) Korean Patent Registration No. 10-1649600 (Title: Moving negative pressure isolation ward system)

SUMMARY

The present disclosure is directed to providing a mobile infectious disease clinic that allows a test subject to be tested by a healthcare provider using an infectious disease test kit while the healthcare provider and the test subject are isolated and that allows disinfection and disinfection completion notification to be automatically performed after testing.

The present disclosure is also directed to providing a mobile infectious disease clinic that allows the internal negative pressure to be adaptively adjusted according to the body temperature of the test subject.

The present disclosure is also directed to providing a mobile infectious disease clinic in which disinfection and indication of whether disinfection is completed are automatically performed.

The present disclosure is also directed to providing a mobile infectious disease clinic that includes an ultraviolet C (UV-C) lamp capable of effectively performing sterilization of an infectious disease, reducing the disinfection time, and adaptively adjusting the light radiation intensity according to whether the body temperature of the test subject is abnormal or a negative pressure device is abnormal.

The present disclosure is also directed to providing a tent-type mobile infectious disease clinic which makes it possible to promptly install a large number of mobile infectious disease clinics due to having mobility and being easy to install and remove.

Various embodiments of the present disclosure provide a mobile infectious disease clinic, which is a tent-type mobile infectious disease clinic, including a tent which is in the form of an isolated space that a test subject is able to enter, the inside of the tent being visible from the outside and the tent partially or entirely including a transparent wall to block the spread of an infectious disease between the inside and the outside of the tent, one or more openings which are disposed in the transparent wall and through which a hand of a healthcare provider outside the tent is able to pass to perform testing for the infectious disease on the test subject, a negative pressure device which is configured to adjust an air pressure in the tent to be lower than an air pressure outside the tent to cause the air outside the tent to enter the tent and configured to filter the air inside the tent and then discharge the filtered air to the outside of the tent, a thermal imaging camera which is configured to measure the body temperature of the test subject in the tent, and a UV-C lamp which is configured to radiate light of a wavelength in a range of 100 nm to 280 nm toward the inside of the tent in order to perform sterilization in the tent, wherein the UV-C lamp is also configured to adjust the radiation intensity of the light to be increased as a difference between the body temperature of the test subject and a set normal body temperature is larger.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Terms used herein are for describing specific embodiments and are not intended to limit the scope of other embodiments. A singular expression may include a plural expression unless the context clearly indicates otherwise. The terms including technical or scientific terms used herein may have the same meaning as commonly understood by those of ordinary skill in the art to which the present disclosure pertains. Among the terms used herein, terms, such as those defined in commonly used dictionaries, may be construed as having a meaning that is the same as or similar to their meaning in the context of the relevant art and are not to be construed in an idealized or overly formal sense unless expressly so defined herein. In some cases, even terms defined herein cannot be construed to exclude embodiments of the present disclosure.

The content of the present disclosure is based on the following research.

[Subject Identification Code] HW20C2103000020

[Name of Ministry] Ministry of Health and Welfare, Ministry of Science and ICT, Ministry of Trade, Industry, and Energy, Ministry of Food and Drug Safety

[Research Project Name] Infectious disease control technology development project

[Research Subject Name] Development of smart algorithm for early screening and diagnosis of patients with symptoms of airborne infectious diseases and prevention of spread of airborne infectious diseases and development of mobile quarantine-associated system

[Specialized Research Management Institution] Korea Medical Device Development Fund

[Contribution Rate] 100% Contribution rate of infectious disease control technology development project

[Research Institution in Charge] Yonsei University-Industry Foundation

[Research Period] Sep. 1, 2020-Dec. 31, 2022

Figure 1:
FIG. 1 illustrates an example of a tent in which a mobile infectious disease clinic is disposed according to various embodiments of the present disclosure.

FIG. 1 illustrates an example of a tent in which a mobile infectious disease clinic is disposed according to various embodiments of the present disclosure.

Referring to FIG. 1, a tent that one adult is able to enter while standing without bending over is illustrated as an example of a tent in which an infectious disease clinic is disposed. The tent of FIG. 1 is only an example, and the form of the tent is not limited. An embodiment of the present disclosure may be applied to any other tent as long as the tent allows a patient or test subject to be isolated therein.

Figure 2:
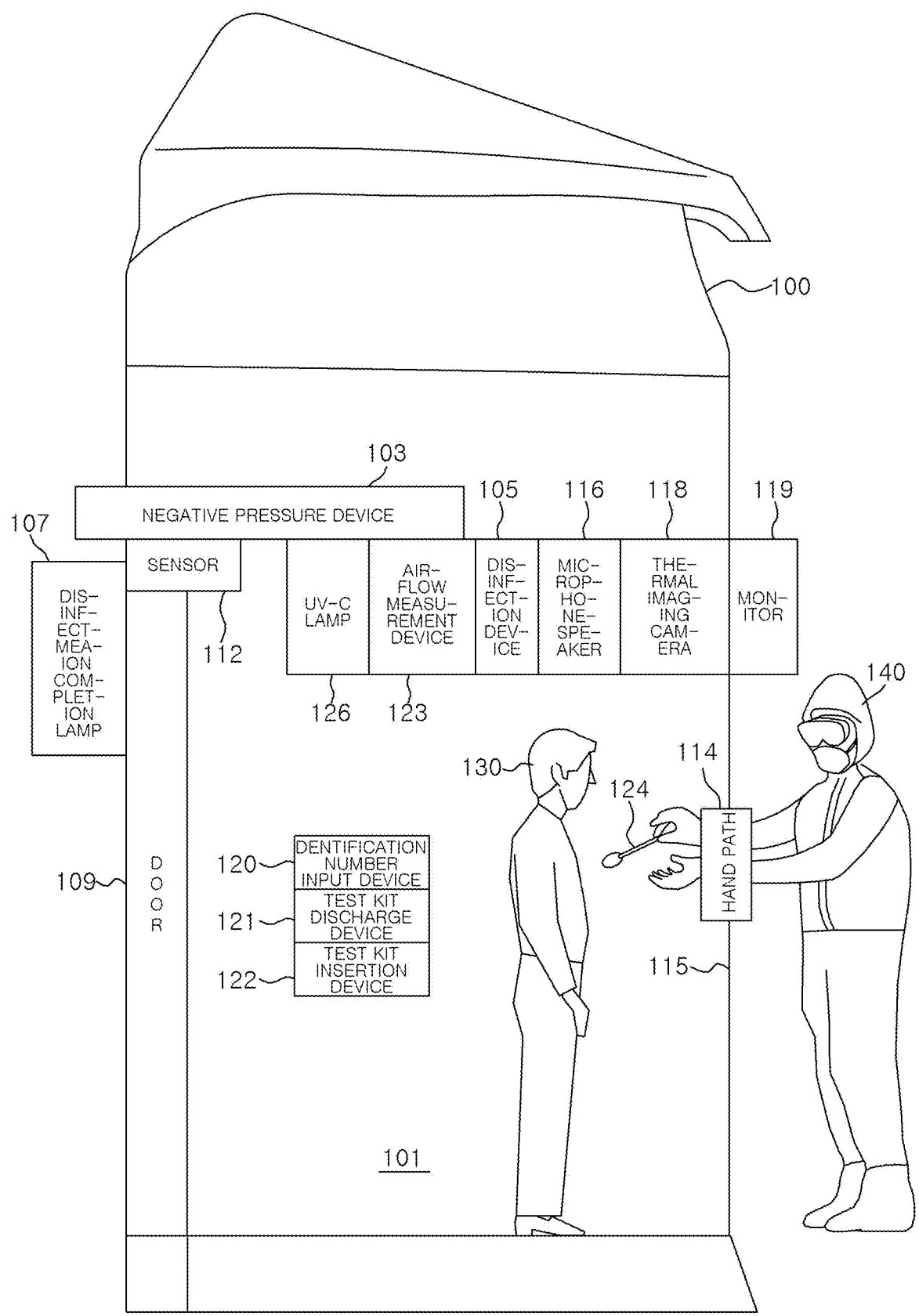
FIG. 2 illustrates a configuration of a mobile infectious disease clinic according to various embodiments of the present disclosure.

FIG. 2 illustrates a configuration of a mobile infectious disease clinic according to various embodiments of the present disclosure.

Referring to FIG. 2, a mobile infectious disease clinic 100 is in the form of a tent. The tent-type mobile infectious disease clinic 100 includes a tent 101 that a test subject 130 is able to enter.

The tent 101 includes a wall 115 that is able to block the spread of an infectious disease between the inside and outside of the tent 101. The wall 115 may be partially or entirely made of a transparent material, such as glass, plastic, or vinyl, through which light may pass. The wall 115 may block a flow of air between the inside and outside of the tent 101 to block the spread of the infectious disease. Since a healthcare provider 140, who performs testing for the infectious disease on the test subject 130, performs testing in a space isolated from the test subject 130, that is, outside the tent 101, the healthcare provider 140 may, without changing into a new protective suit after testing, immediately perform the next testing while wearing a protective suit worn during the previous testing. Since light passes through the wall 115, the healthcare provider 140 may perform testing while looking at the test subject 130 through the wall 115.

One or more openings 114 through which a hand of the healthcare provider 140 may pass are disposed in the wall 115.

According to various embodiments of the present disclosure, the one or more openings 114 may be opened and closed. Therefore, when performing testing, the healthcare provider 140 may open the one or more openings 114 to put his or her hand into the tent 101. Also, after the testing is finished, the healthcare provider 140 may close the one or more openings 114. By the one or more openings 114, which may be opened and closed, being opened only when performing testing in order to allow a hand of the healthcare provider 140 to enter and being closed at other times, a flow of air between the inside and outside of the tent 101 may be blocked. After testing, the healthcare provider 140 may only replace a glove surrounding the hand that has entered the tent 101 through the one or more openings 114 and may not replace the protective suit that has not come into contact with the air inside the tent 101. In conventional infectious disease testing clinics, since the test subject 130 and the healthcare provider 140 are exposed to the same space, the healthcare provider 140 has to replace the protective suit after each testing, which consumes cost and time and exhausts physical strength of the healthcare provider 140. However, according to various embodiments of the present disclosure, since the healthcare provider 140 only needs to replace the glove after testing, it is possible to save cost, time, and the physical strength of the healthcare provider 140 that may be wasted due to replacing the protective suit.

According to various embodiments of the present disclosure, one or more gloves that the hands of the healthcare provider 140 outside the tent 101 may enter may be disposed from the one or more openings 114 toward the inside of the tent 101. The one or more gloves may be made of a material, such as rubber, latex, and plastic, which blocks contact with air. Due to the one or more gloves, a flow of air through the one or more openings 114 may be blocked. Even when the healthcare provider 140 puts his or her hand in the one or more gloves, the hand of the healthcare provider 140 may not come in contact with the air inside the tent 101. Therefore, since no part of the body of the healthcare provider 140 comes in contact with the air inside the tent 101, the healthcare provider 140 may not replace the gloves as well as the protective suit after testing. Therefore, according to various embodiments of the present disclosure, since the healthcare provider 140 may not replace anything after testing, it is possible to save the cost, time, and physical strength of the healthcare provider 140 that may be wasted due to replacing the protective suit and gloves.

According to various embodiments of the present disclosure, an ultraviolet C (UV-C) lamp 126 may be disposed in the tent 101. The UV-C lamp 126 may be configured to radiate light of a wavelength in a range of 100 nm to 280 nm toward the inside of the tent 101 in order to perform sterilization in the tent 101. The UV-C lamp 126 may also be configured to adaptively adjust the radiation intensity of the light on the basis of a difference between the body temperature of the test subject 130 and a set normal body temperature. The UV-C lamp 126 may also be configured to adjust the light radiation intensity to be increased as a difference between the body temperature of the test subject 130 and the set normal body temperature is larger. The normal body temperature may be set to be 36.5° C., which is normal human body temperature. Alternatively, the normal body temperature may be set to be in a predetermined temperature range around 36.5° C., e.g., a range from 36.0° C. to 37.0° C. The larger the difference between the body temperature of the test subject 130 and the set normal body temperature, the higher the likelihood of detecting an abnormal symptom due to an infectious disease or the like from the test subject 130. Therefore, the larger the difference between the body temperature of the test subject 130 and the set normal body temperature, the stronger the sterilization for air that has come into contact with the test subject 130 should be. Through such a configuration, it is not necessary to maintain the output of the first UV-C lamp 126 to be maximum at all times, and by adaptively adjusting the output of the first UV-C lamp 126, the first UV-C lamp 126 may be efficiently operated.

According to various embodiments of the present disclosure, a switch 111 to which a start or an end of testing of the test subject 130 is input may be disposed outside the tent 101. The switch 111 may be directly pressed by the healthcare provider 140 prior to the start of testing or after the testing is finished. By the healthcare provider 140 pressing the switch 111, the start or end of the testing may be clearly input.

A disinfection device 105 configured to spray a disinfectant inside the tent 101 upon an input of the end of testing to the switch 111 may be disposed inside the tent 101. A disinfection completion lamp 107 configured to be turned on to indicate disinfection completion after an elapse of a set amount of time from the time when the end of testing is input to the switch 111 may be disposed outside the tent 101.

According to various embodiments of the present disclosure, a door 109 through which the test subject 130 is able to enter the tent 101 may be disposed. The door 109 may be configured to be open upon an input of the start of testing to the switch 111 and be locked upon the input of the end of testing to the switch 111 in a state in which the disinfection completion lamp 107 is turned on.

According to various embodiments of the present disclosure, a sensor 112 configured to determine whether the person 130 is present in the tent 101 may be disposed in the tent 101. Also, the switch 111 may be configured to receive an input indicating the end of testing when the sensor 112 has determined that the person 130 is not present in the tent 101.

When the end of testing is input to the switch 111 by the healthcare provider 140 in a state in which the sensor 112 has determined that the person 130 is not present in the tent 101, the door 109 is locked, and disinfection of the tent 101 by the disinfection device 105 starts.

The disinfection of the inside of the tent 101 by the disinfection device 105 continues for a set disinfection time. For example, the set disinfection time may be set as an arbitrary amount of time in a range of 10 minutes to 30 minutes.

According to various embodiments of the present disclosure, the disinfection time during which the disinfection device 105 sprays the disinfectant may be set to be shorter as the intensity of light radiated by the UV-C lamp 126 while the disinfection device 105 sprays the disinfectant is higher. Since the light of the wavelength in the range of 100 nm to 280 nm that is radiated by the UV-C lamp 126 has a sterilizing effect, the same or similar disinfection result may be achieved even when the disinfection time is reduced as the light radiation intensity is higher.

While the disinfection of the inside of the tent 101 is performed by the disinfection device 105, the disinfection completion lamp 107 is in a turned-off state, the start of testing is not input even when the switch 111 is pressed, and the door 109 maintains a locked state.

After a set amount of time from the start of disinfection has elapsed, the disinfection completion lamp 107 is turned on to indicate disinfection completion. The lighting of the disinfection completion lamp 107 indicates that the mobile infectious disease clinic 100 is available.

When the start of testing is input to the switch 111 by the healthcare provider 140 in a state in which the disinfection completion lamp 107 is turned on, the door 109 is opened, and the disinfection completion lamp 107 is turned off.

According to various embodiments of the present disclosure, a first microphone-speaker 116 may be disposed inside the tent 101, and a second microphone-speaker 106 may be disposed outside the tent 101. Since the test subject 130 and the healthcare provide 140 are blocked from each other by the wall 115, their voices are not able to directly reach one another. The test subject 130 and the healthcare provider 140 may communicate using the first microphone-speaker 116 and the second microphone-speaker 106.

According to various embodiments of the present disclosure, an identification number input device 120 configured to receive an identification number of the test subject 130, e.g., the resident registration number of the test subject 130, via a key input or a voice input may be disposed in the tent 101. Also, a test kit discharge device 121 configured to, in response to the input of the identification number, discharge a test kit 124 with personal information of the test subject 130, e.g., name, gender, and age of the test subject 130, indicated thereon may be disposed in the tent 101. Also, a test kit insertion device 122 configured to insert the test kit 124 after testing for an infectious disease on the test subject 130 is performed using the test kit 124 may be disposed in the tent 101.

In FIG. 2, the identification number input device 120, the test kit discharge device 121, and the test kit insertion device 122 are illustrated as being located behind the test subject 130. However, according to various embodiments of the present disclosure, the identification number input device 120, the test kit discharge device 121, and the test kit insertion device 122 may be disposed at any other position in the tent 101.

The test subject 130 directly inputs his or her identification number, e.g., his or her resident registration number, into the identification number input device 120 according to his or her own will. The identification number input device 120 may receive the identification number via a key input using a touchpad, a physical keyboard, and the like. Alternatively, the identification number input device 120 may provide guidance in the form of audio or display to the test subject 130 so that the test subject 130 inputs his or her identification number, and then, when the test subject 130 says his or her identification number out loud, the identification number input device 120 may identify this and receive the identification number of the test subject 130.

When the identification number of the test subject 130 is input to the identification number input device 120, the test kit 124 with personal information of the test subject 130, e.g., name, gender, and age of the test subject 130, indicated thereon is discharged from the test kit discharge device 121. The test subject 130 directly takes out the test kit 124 from the test kit discharge device 121 and then passes the test kit 124 to the hand of the healthcare provider 140. The healthcare provider 140 may put his or her hand in the tent 101 through the one or more openings 114. Therefore, the test subject 130 may pass the test kit 124 to the hand of the healthcare provider 140 that enters the tent 101 through the one or more openings 114.

The healthcare provider 140 may hold the test kit 124 by the hand put inside the tent 101 through the one or more openings 114 and perform testing for an infectious disease on the test subject 130. According to various embodiments of the present disclosure, light may pass through the wall 115. Also, according to various embodiments of the present disclosure, the healthcare provider 140 and the test subject 130 may communicate using the first microphone-speaker 116 and the second microphone-speaker 106. Therefore, the healthcare provider 140 may perform testing for an infectious disease on the test subject 130.

The healthcare provider 140 may pass the test kit 124 to the test subject 130 after the testing for an infectious disease is finished, and the test subject 130 may directly insert the test kit 124 into the test kit insertion device 122. The test kit 124 inserted into the test kit insertion device 122 is discharged to the outside of the mobile infectious disease clinic 100 and used in analysis of the result of testing the test subject 130.

According to various embodiments of the present disclosure, a thermal imaging camera 118 configured to measure the body temperature of the test subject 130 in the tent 101 may be disposed inside the tent 101.

According to various embodiments of the present disclosure, a monitor 119 configured to display the body temperature of the test subject 130 that is measured by the thermal imaging camera 118 may be disposed outside the tent 101. The healthcare provider 140 may check the body temperature of the test subject 130 through the monitor 119 and primarily determine whether the test subject has any abnormal symptom such as fever.

According to various embodiments of the present disclosure, a negative pressure device 103 which is configured to adjust an air pressure in the tent 101 to be lower than an air pressure outside the tent 101 to cause the air outside the tent 101 to enter the tent 101 and configured to filter the air inside the tent 101 and then discharge the filtered air to the outside of the tent 101 may be disposed at the tent 101.

According to various embodiments of the present disclosure, the negative pressure device 103 may also be configured to adaptively adjust the air pressure in the tent 101 on the basis of a difference between the body temperature of the test subject 130 and the set normal body temperature. The normal body temperature may be set to be 36.5° C., which is normal human body temperature. Alternatively, the normal body temperature may be set to be in a predetermined temperature range around 36.5° C., e.g., a range from 36.0° C. to 37.0° C.

According to various embodiments of the present disclosure, the negative pressure device 103 may also be configured to adjust a negative pressure difference between the air pressure in the tent 101 and the air pressure outside the tent 101 to be increased as the difference between the body temperature of the test subject 130 and the set normal body temperature is larger. The larger the difference between the body temperature of the test subject 130 and the set normal body temperature, the higher the likelihood of detecting an abnormal symptom due to an infectious disease or the like from the test subject 130. Therefore, it is necessary to more strongly prevent the flow of air, which has come into contact with the test subject 130, to the outside of the tent 101 as the difference between the body temperature of the test subject 130 and the set normal body temperature is larger. Through such a configuration, it is not necessary to maintain the output of the negative pressure device 103 to be maximum at all times, and by adaptively adjusting the output of the negative pressure device 103, the negative pressure device 103 may be efficiently operated.

According to various embodiments of the present disclosure, when the difference between the body temperature of the test subject 130 and the set normal body temperature is over a set range, the negative pressure device 103 may also be configured to adjust a ratio, at which the negative pressure difference between the air pressure in the tent 101 and the air pressure outside the tent 101 is increased as the intensity of light radiated by the UV-C lamp 126 is higher, to be decreased. Since the effect of sterilizing the air inside the tent 101 is greater as the intensity of light radiated by the UV-C lamp 126 is higher, it is possible to prevent the outflow of an infectious disease even when a ratio at which the output of the negative pressure device 103 is increased is adjusted to be relatively lower.

According to various embodiments of the present disclosure, a first airflow measurement device 123 may be disposed in the tent 101. The first airflow measurement device 123 may be configured to measure a direction or velocity of an airflow in the tent 101 that is caused by the negative pressure device 103. The first airflow measurement device 123 may include a display, and the display may be configured to display the measured direction or velocity of the airflow. The display may also be configured to display abnormal operation of the negative pressure device 103 in a case where the measured direction of the airflow is different from a set direction, e.g., a direction from the outside to the inside of the tent 101, or the measured velocity of the airflow is below a set normal velocity range.

According to various embodiments of the present disclosure, in the case where the direction of airflow measured by the first airflow measurement device 123 is different from a set direction or the measured velocity of the airflow is below a set normal velocity range, the negative pressure device 103 may be seen as not functioning correctly, and there is a possibility of the spread of an infectious disease due to the outflow of air that has come into contact with the test subject 130. Therefore, for strong sterilization of the air that has come into contact with the test subject 130, in this case, the UV-C lamp 126 may also be configured to adjust the light radiation intensity to become higher than or equal to a set radiation intensity.

Although not shown in FIG. 2, according to various embodiments of the present disclosure, the mobile infectious disease clinic 100 may further include a processor and a memory.

The processor is electrically connected to each component of the mobile infectious disease clinic, and may control each component so that each component operates as proposed in various embodiments of the present disclosure. The processor may include at least one processor.

The memory may be electrically connected to each component of the mobile infectious disease clinic 100, and may store information measured in each component or information related to an operation of each component. In addition, the memory may be electrically connected to the processor and store data such as a basic program for operation of the processor, an application program, setting information, and information generated by operation of the processor. The memory may be comprised of a volatile memory, a nonvolatile memory, or a combination of volatile and nonvolatile memory. In addition, the memory may provide stored data according to a request of the processor.

Figure 3:
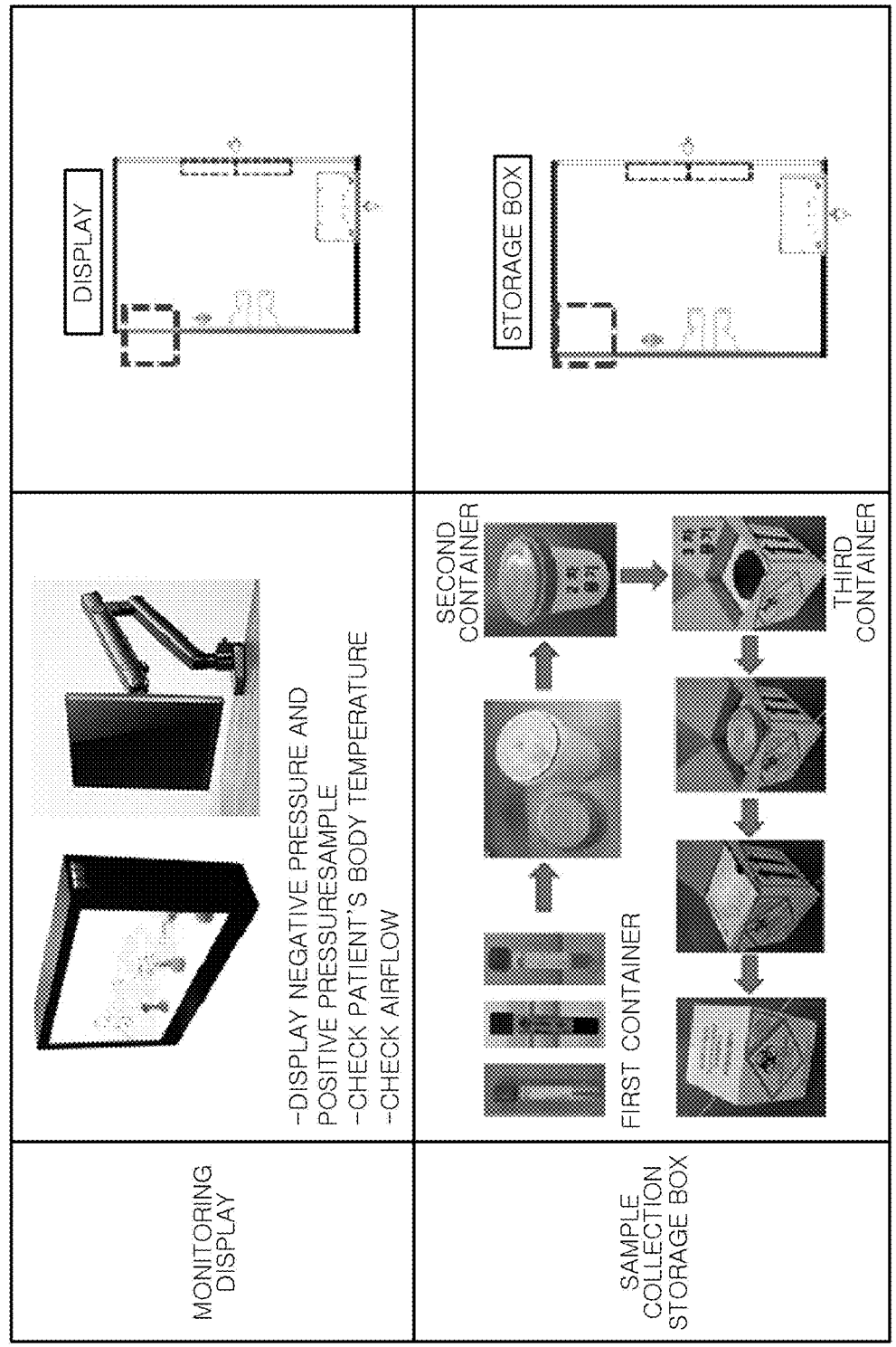
FIG. 3 illustrates a configuration of a mobile infectious disease clinic according to various embodiments of the present disclosure.

FIG. 3 illustrates components in a mobile infectious disease clinic according to various embodiments of the present disclosure. Specifically, FIG. 3 illustrates a monitoring display and a sample collection storage box.

Referring to FIG. 3, the monitoring display is disposed to be viewed by the healthcare provider. The monitoring display may display a negative pressure state in the tent where the test subject is located, the body temperature of the test subject, an airflow state inside the tent, and the like.

The sample collection storage box is a storage box for holding a sample collected from the test subject. According to an embodiment, the sample collection storage box may be formed of a multi-layer packaging structure to prevent the spread of an infectious disease. For example, the sample collection storage box may be formed of a structure including a first container configured to hold an initially-collected sample, a second container configured to hold the first container, and a third container configured to hold the second container.

Figure 4:
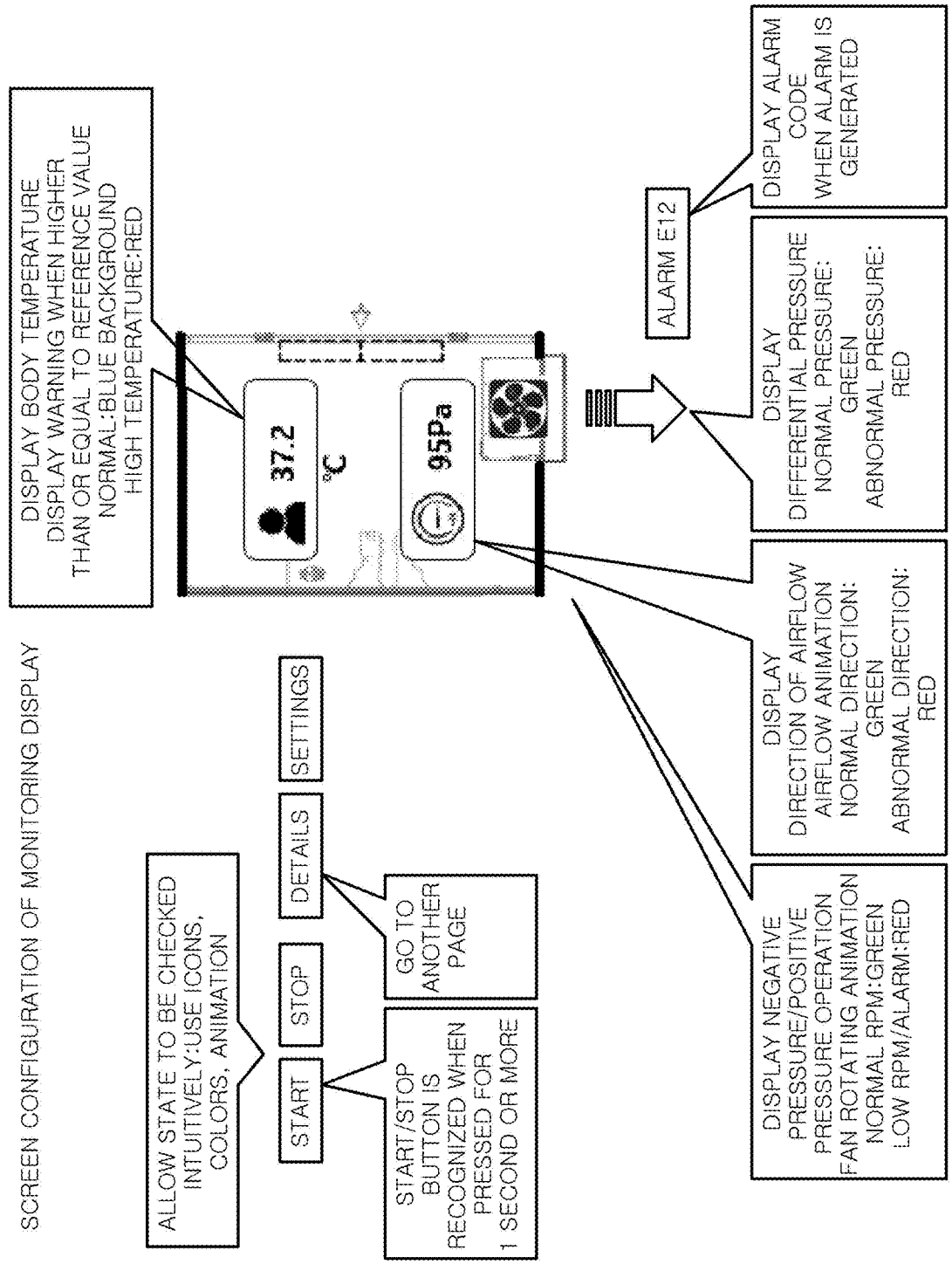
FIG. 4 illustrates a screen configuration of a monitoring display according to various embodiments of the present disclosure.

FIG. 4 illustrates a screen configuration of a monitoring display according to various embodiments of the present disclosure. Specifically, FIG. 4 illustrates an example of a display screen of the monitoring display disposed to be viewed by the healthcare provider.

Referring to FIG. 4, the monitoring display may display the body temperature of the test subject, a difference between air pressures outside and inside the tent where the test subject is located, that is, a differential pressure, an operational state of the negative pressure device in the tent, and whether an abnormality occurs, for example, whether the body temperature of the test subject is abnormal, the differential pressure is abnormal, or an abnormality occurs during the operation of the negative pressure device. Also, the healthcare provider may manipulate the operation of the negative pressure device through the monitoring display.

The monitoring display may utilize icons, colors, animation, or the like to allow a state to be checked intuitively. The body temperature may be displayed in blue when normal, displayed in red when high, and displayed with a warning when higher than or equal to a reference value. The differential pressure may be displayed in green when normal and displayed in red when abnormal. The airflow direction may be displayed with animation and may be displayed in green when the airflow direction due to the negative pressure device is normal and displayed in red when the airflow direction is abnormal. The operation of the negative pressure device may be displayed in the form of fan rotating animation and may be displayed in green when the revolutions per minute (RPM) of the negative pressure device is normal and displayed in red with an alarm when the RPM is low. When the alarm is generated, an alarm code for indicating the reason for the alarm may be displayed. The start or stop of the operation of the negative pressure device may be manipulated by a touch input on the monitoring display which is formed of a touch display.

Figure 5:
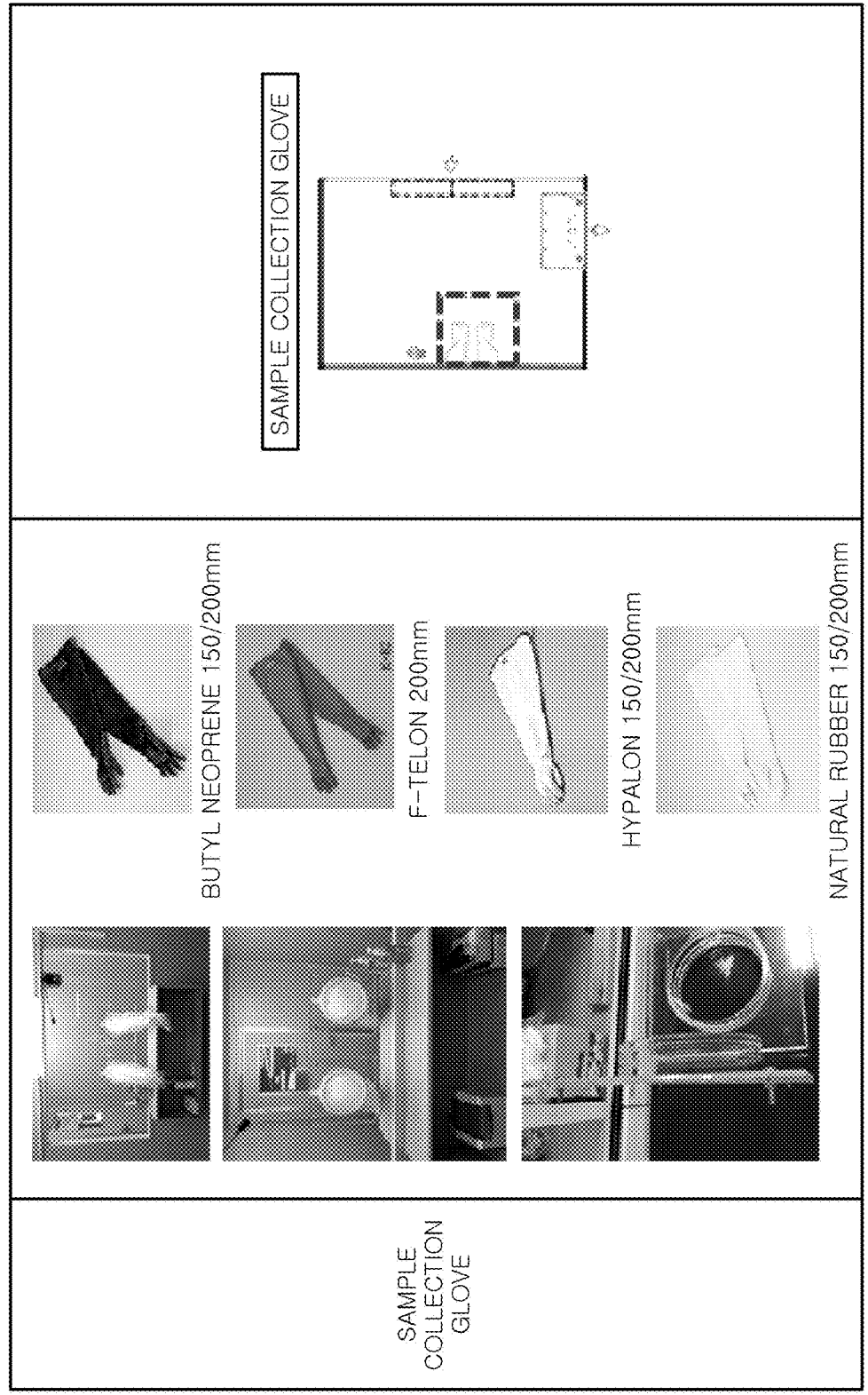
FIG. 5 illustrates components in a mobile infectious disease clinic according to various embodiments of the present disclosure.

FIG. 5 illustrates components in a mobile infectious disease clinic according to various embodiments of the present disclosure. Specifically, FIG. 5 illustrates examples of a sample collection glove disposed at the opening in the partition between the inside of the tent where the test subject is located and the outside of the tent where the healthcare provider is located.

Referring to FIG. 5, the sample collection glove may be made of a material through which air does not pass in order to block the spread of an infectious disease. The sample collection glove may be made of various materials such as a synthetic fiber or rubber.

Figure 6:
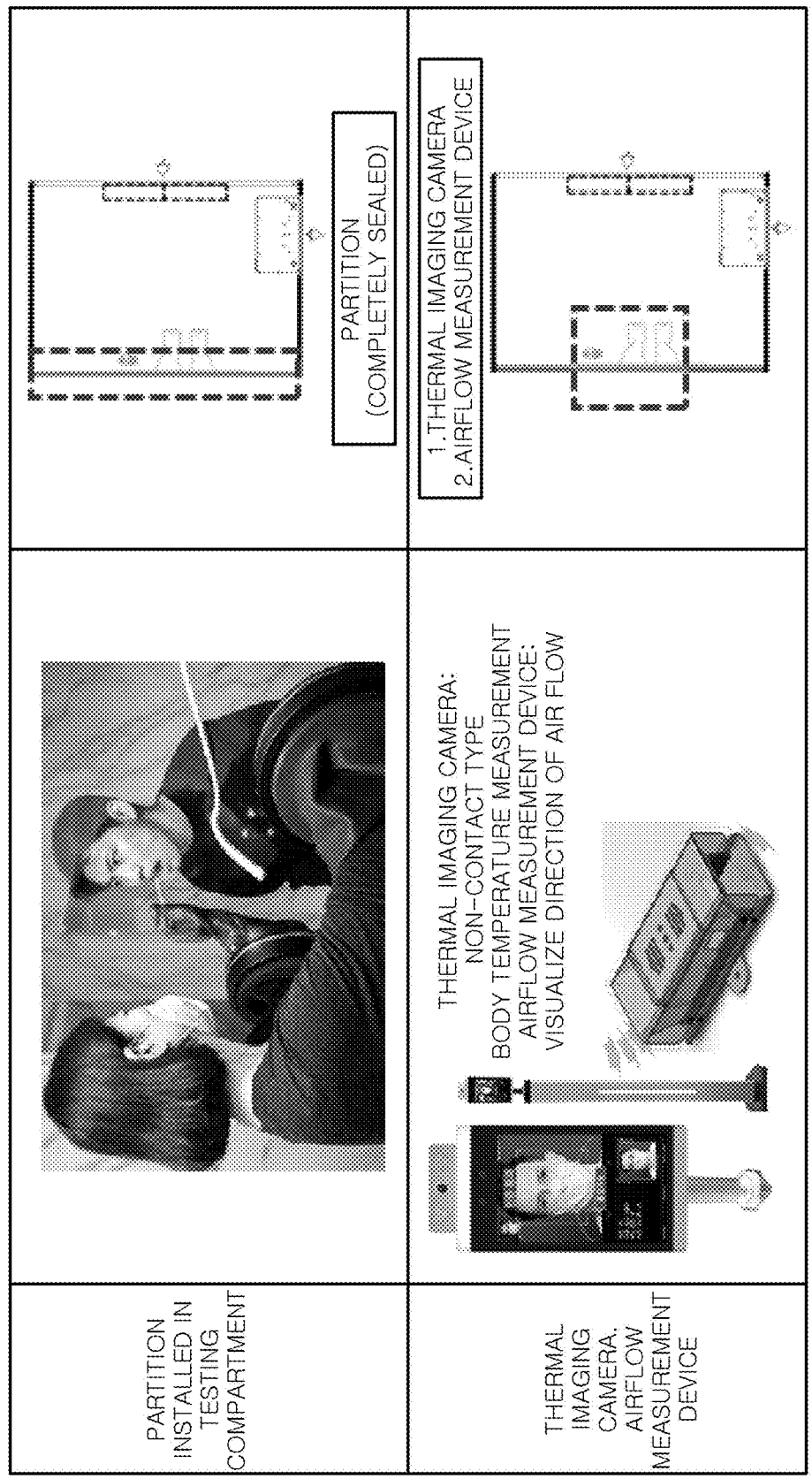
FIG. 6 illustrates components in a mobile infectious disease clinic according to various embodiments of the present disclosure.

FIG. 6 illustrates components in a mobile infectious disease clinic according to various embodiments of the present disclosure. Specifically, FIG. 6 illustrates the partition between the inside of the tent where the test subject is located and the outside of the tent where the healthcare provider is located, the thermal imaging camera installed in the tent, and the airflow measurement device configured to measure the direction and velocity of an airflow due to the negative pressure device.

Referring to FIG. 6, the partition is disposed between the inside of the tent and the outside of the tent and prevents the spread of an infectious disease by completely sealing the inside of the tent and the outside of the tent from each other. The healthcare provider may use the thermal imaging camera, the airflow measurement device, etc. to check the state in the tent where the test subject is located.

The thermal imaging camera may measure the body temperature of the test subject from an image of the face of the test subject. That is, the thermal imaging camera may measure the body temperature of the test subject without coming in contact with the test subject.

The airflow measurement device may measure the direction and velocity of an airflow due to the negative pressure device and visually display the direction of the airflow.

Figure 7:
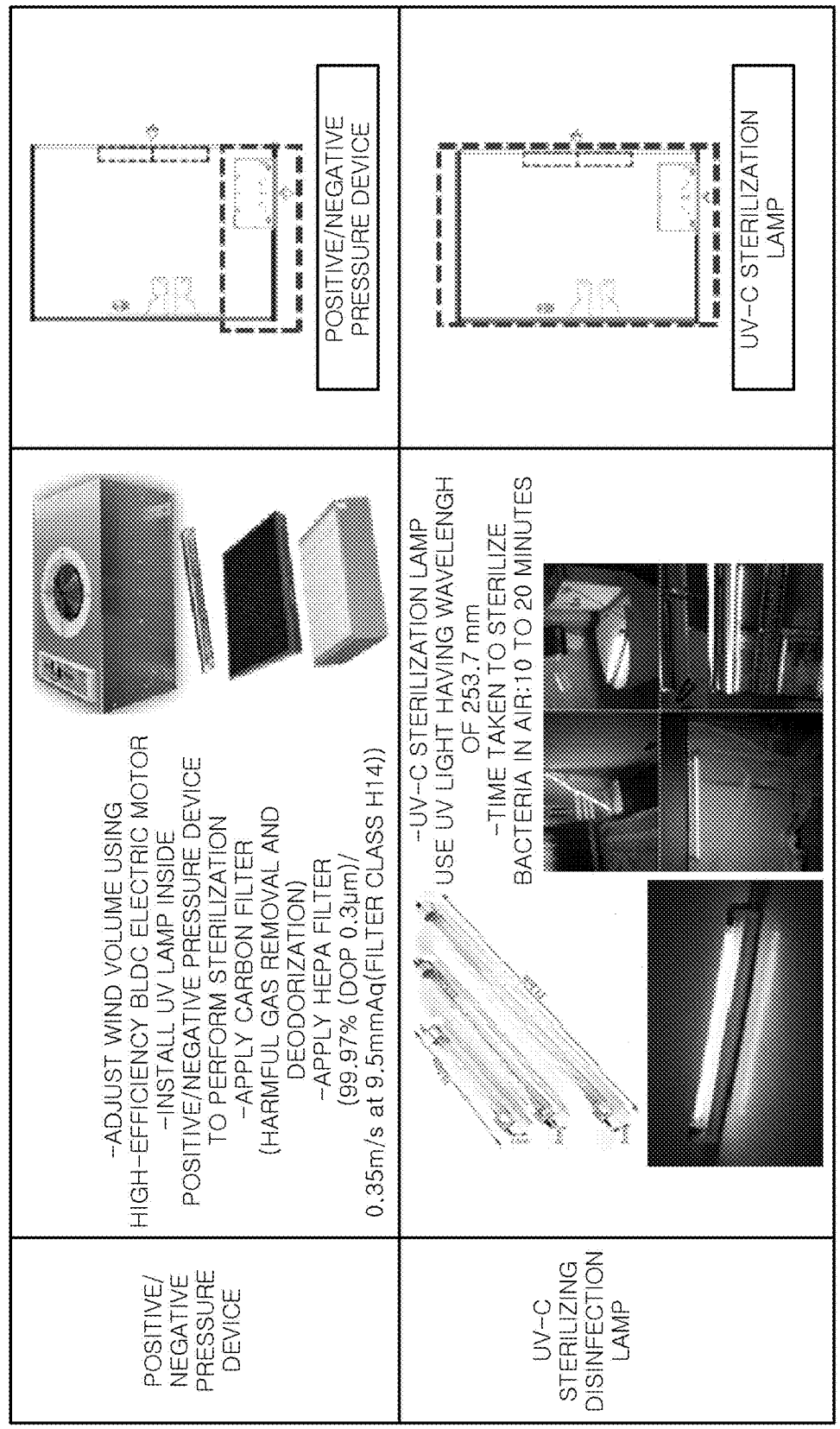
FIG. 7 illustrates components in a mobile infectious disease clinic according to various embodiments of the present disclosure.

FIG. 7 illustrates components in a mobile infectious disease clinic according to various embodiments of the present disclosure. Specifically, FIG. 7 illustrates the negative pressure device disposed in the tent where the test subject is located and the UV-C lamp for sterilization and disinfection.

Referring to FIG. 7, the negative pressure device may adjust a wind volume using a high-efficiency brushless direct current (BLDC) electric motor. Also, a UV lamp may be installed inside the negative pressure device to introduce or discharge air that is primarily sterilized. Also, the negative pressure device may apply a carbon filter to perform a harmful gas removal function and a deodorization function. Also, the negative pressure device may use a high-efficiency particulate air (HEPA) filter to operate with 99.97% blocking effect for 0.3-μm dispersed oil particulate (DOP) and operate with 0.35 m/s at 9.5 mmAq (filter class H14).

The UV-C lamp may use light of a wavelength in a range of 100 nm to 280 nm, e.g., light of a wavelength of 253.7 nm, to perform sterilization for air in the mobile infectious disease clinic. Using the UV-C lamp, it is possible to sterilize bacteria in the air within 10 to 20 minutes.

Figure 8:
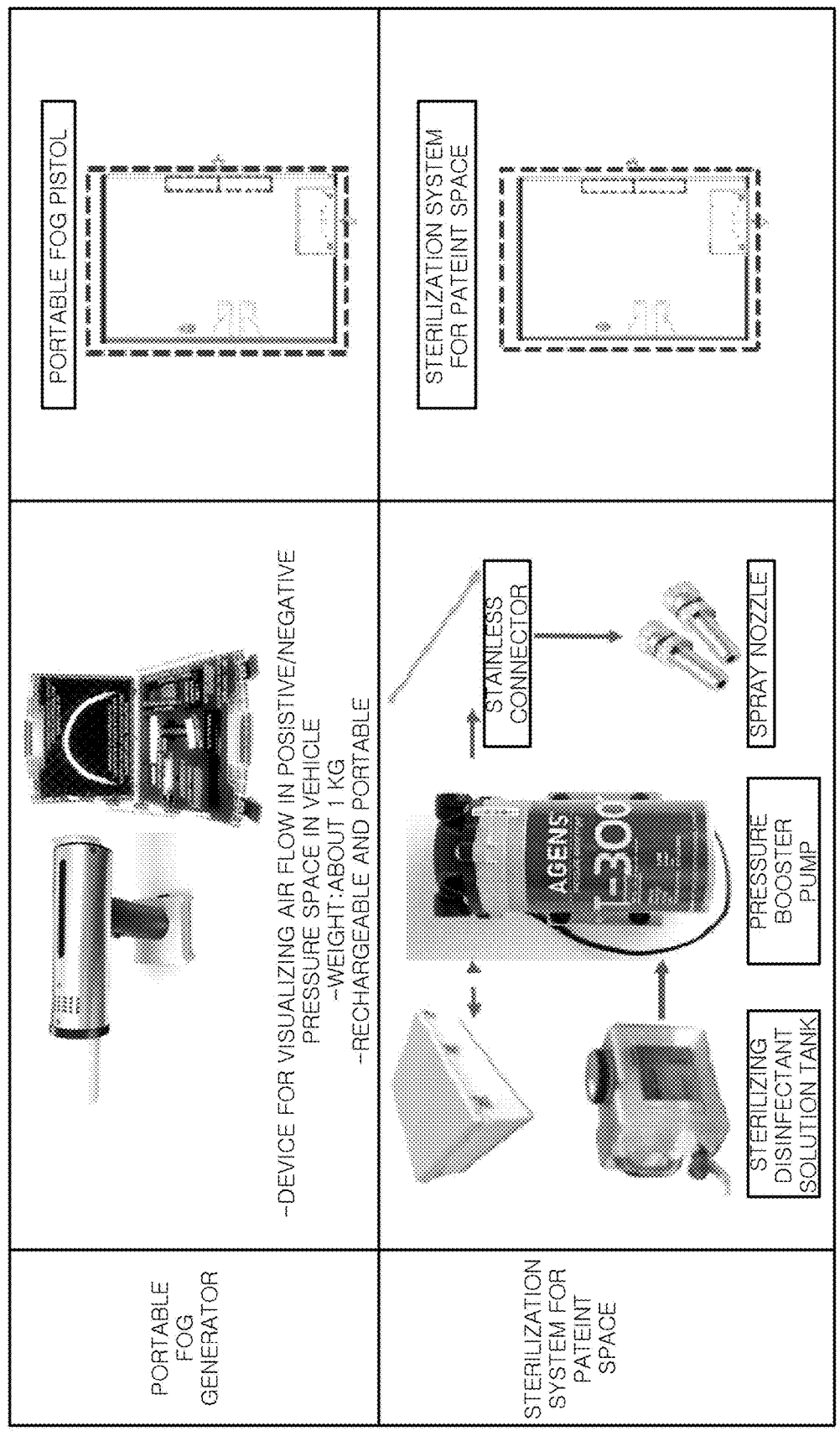
FIG. 8 illustrates components in a mobile infectious disease clinic according to various embodiments of the present disclosure.

FIG. 8 illustrates components in a mobile infectious disease clinic according to various embodiments of the present disclosure. Specifically, FIG. 8 illustrates a fog generator for airflow measurement and a sterilization system in the tent where a patient or test subject is located.

Referring to FIG. 8, the fog generator may spray fog to visualize an air flow related to a negative pressure space inside the tent. The fog generator may be rechargeable and portable.

In the sterilization system, a disinfectant solution in a sterilizing disinfectant solution tank is injected with a pressure booster pump, and according to manipulation of a control box, the disinfectant solution is sprayed from a spray nozzle through a stainless connector. By automatically spraying the disinfectant solution through the sterilization system to a space the test subject has exited after sample collection, it is possible to automatically perform disinfection without a person entering the space.

The present disclosure can provide a mobile infectious disease clinic that allows a test subject to be tested by a healthcare provider using an infectious disease test kit while the healthcare provider and the test subject are isolated and that allows disinfection and disinfection completion notification to be automatically performed after testing. Accordingly, the time taken for disinfection of the clinic can be efficiently utilized. Further, since testing is performed while the healthcare provider and the test subject are isolated and exposure of the body parts is minimized, it is possible to save cost, time, and physical strength of the healthcare provider that are necessary for the healthcare provider to change into a new protective suit after each testing.

The present disclosure can also provide a mobile infectious disease clinic that allows the internal negative pressure to be adaptively adjusted according to the body temperature of the test subject. Accordingly, since, in the case of a patient with fever, etc. who is likely to be tested positive for the disease, it is possible to adaptively adjust the negative pressure so that the negative pressure can be increased to be higher than usual, a negative pressure device can be efficiently operated.

The present disclosure can also provide a mobile infectious disease clinic cluster in which disinfection and indication of whether disinfection is completed are automatically performed. Accordingly, the time taken for disinfection of the mobile infectious disease clinics can be efficiently used. Also, by continuously providing an available mobile infectious disease clinic, the number of tests performed can be maximized using the least possible number of healthcare providers within a limited amount of time.

The present disclosure can also provide a mobile infectious disease clinic that includes a UV-C lamp capable of effectively performing sterilization of an infectious disease, reducing the disinfection time, and adaptively adjusting the light radiation intensity according to whether the body temperature of the test subject is abnormal or the negative pressure device is abnormal. Accordingly, sterilization of an infectious disease can be effectively performed, the disinfection time can be reduced, the UV-C lamp can be efficiently operated, and when an abnormality occurs in the negative pressure device, by performing sterilization before the infectious disease spreads outside the clinic, the spread of the infectious disease through air can be minimized.

The present disclosure can also provide a tent-type mobile infectious disease clinic which has mobility and is easy to install and remove. Accordingly, by promptly installing a large number of mobile infectious disease clinics, the number of tests performed for the infectious disease can be increased, and the spread of the infectious disease can be effectively prevented.

The advantageous effects of the present disclosure are not limited to those mentioned above, and other unmentioned advantageous effects should be clearly understood by those of ordinary skill in the art to which the present disclosure pertains from the description herein.

In specific embodiments of the present disclosure described above, elements included in the disclosure have been expressed as singular or plural according to the proposed specific embodiment. However, a singular or plural expression has been selected to be suitable for a proposed situation for convenience of description, and the present disclosure is not limited by the singular or plural elements. An element expressed as plural may also be configured to be singular, and likewise, an element expressed as singular may also be configured to be plural.

Meanwhile, in the detailed description of the present disclosure, specific embodiments have been described, but of course, various modifications are possible within the scope not departing from the scope of the present disclosure. Therefore, the scope of the present disclosure should not be defined as being limited by the embodiments described herein and should be defined by the scope of the claims as well as their equivalents.

What is claimed is:

1. A mobile infectious disease clinic, which is a tent-type mobile infectious disease clinic, comprising:
    a tent which is in a form of an isolated space that a test subject is able to enter, an inside of the tent being visible from an outside of the tent, the tent partially or entirely including a transparent wall to block a spread of an infectious disease between the inside and the outside of the tent;
    one or more openings which are disposed in the transparent wall and through which a hand of a healthcare provider outside the tent is able to pass to perform testing for the infectious disease on the test subject;
    a negative pressure device which is configured to adjust an air pressure in the tent to be lower than an air pressure outside the tent to cause the air outside the tent to enter the tent and configured to filter the air inside the tent and then discharge the filtered air to the outside of the tent;
    a thermal imaging camera which is configured to measure a body temperature of the test subject in the tent;
    a UV-C lamp which is configured to radiate light of a wavelength in a range of 100 nm to 280 nm toward the inside of the tent in order to perform sterilization in the tent,
    wherein the UV-C lamp is further configured to adaptively adjust a radiation intensity of the light based on a difference between the body temperature of the test subject and a set normal body temperature,
    wherein the UV-C lamp is further configured to adjust the radiation intensity of the light to be increased as a difference between the body temperature of the test subject and a set normal body temperature is larger;
    an airflow measurement device configured to measure a direction or a velocity of an airflow in the tent that is caused by the negative pressure device,
    wherein the airflow measurement device includes a display, and
    wherein the display is configured to display the measured direction or the velocity of the airflow,
    wherein the display is further configured to display abnormal operation of the negative pressure device in a case where the measured direction of the airflow is different from a set direction or the measured velocity of the airflow is below a set normal velocity range,
    wherein, in a case where the measured direction of the airflow is different from a set direction or the measured velocity of the airflow is below a set normal velocity range, the UV-C lamp is also configured to adjust the radiation intensity of the light to be increased to be higher than or equal to a set radiation intensity;
    a switch to which a start or end of testing on the test subject is input;
    a disinfection device configured to spray a disinfectant in the tent for a set disinfection time when the end of the testing is input to the switch; and
    a display configured to indicate whether disinfection is completed after an elapse of the set disinfection time from when the end of the testing is input to the switch,
    wherein the disinfection time is set as an arbitrary amount of time in a configured time range,
    wherein the disinfection time is set to be shorter as the intensity of light radiated by the UV-C lamp while the disinfection device sprays the disinfectant is higher.

2. The mobile infectious disease clinic of claim 1, wherein the negative pressure device is also configured to adjust a negative pressure difference between the air pressure in the tent and the air pressure outside the tent to be increased as the difference between the body temperature of the test subject and the set normal body temperature is larger.

3. The mobile infectious disease clinic of claim 2, wherein, when the difference between the body temperature of the test subject and the set normal body temperature is over a set range, the negative pressure device is also configured to adjust a ratio, at which the negative pressure difference between the air pressure in the tent and the air pressure outside the tent is increased as the intensity of the light radiated by the UV-C lamp is higher, to be decreased.

4. The mobile infectious disease clinic of claim 1, further comprising one or more gloves which are disposed from the one or more openings toward the inside of the tent, wherein the one or more gloves allow a hand of the healthcare provider to enter, and are made of a material that is able to block a flow of air.

* * * * *